US00RE47706E

(19) United States
(12) Reissued Patent
Ohnemus

(10) Patent Number: US RE47,706 E
(45) Date of Reissued Patent: Nov. 5, 2019

(54) SYSTEM AND APPARATUS FOR THE REMOTE ANALYSIS OF CHEMICAL COMPOUND MICROARRAYS

(71) Applicant: dacadoo ag, Zurich (CH)

(72) Inventor: Peter Ohnemus, Herrliberg (CH)

(73) Assignee: dacadoo ag, Zurich (CH)

(21) Appl. No.: 15/332,685

(22) Filed: Oct. 24, 2016

Related U.S. Patent Documents

Reissue of:
(64) Patent No.: 8,873,815
Issued: Oct. 28, 2014
Appl. No.: 13/369,100
Filed: Feb. 8, 2012

U.S. Applications:
(60) Provisional application No. 61/440,748, filed on Feb. 8, 2011.

(51) Int. Cl.
*G06F 9/00* (2006.01)
*C40B 30/02* (2006.01)
(Continued)

(52) U.S. Cl.
CPC ..... *G16B 35/00* (2019.02); *G06T 7/0012* (2013.01); *G16B 25/00* (2019.02); *G16C 20/60* (2019.02);
(Continued)

(58) Field of Classification Search
CPC ..... G40B 30/02; G06T 7/0012; G06T 2207/30072; G06T 2207/10024; G06F 19/20; G06F 19/709; H04N 1/6033
See application file for complete search history.

(56) References Cited

U.S. PATENT DOCUMENTS 5,716,785 A 2/1998 Van Gelder et al.
5,807,522 A 9/1998 Brown et al.
(Continued)

FOREIGN PATENT DOCUMENTS

WO WO 02/093453 11/2002

OTHER PUBLICATIONS

Gulnaz Stybayeva, Onur Mudanyali, Sungkyu Seo, Jaime Silangcruz, Monica Macal, Erlan Ramanculov, Satya Dandekar, Anthony Erlinger, Aydogan Ozcan, and Alexander Revzin "Lensfree Holographic Imaging of Antibody Microarray for High-Throughout Detection of Leukocyte Numbers and Function" Anal. Chem , 82, 3736-3744, May 1, 2010.

(Continued)

*Primary Examiner* — Colin M LaRose
(74) *Attorney, Agent, or Firm* — Leason Ellis LLP

(57) ABSTRACT

A remote microarray analysis system, method and apparatus for use in the remote analysis of a chemical compound microarray supported on a substrate is disclosed. Pixel image data is received from a remote location including image data that depicts (a) a calibration scale associated with the substrate and (b) the microarray. A transformation action of said pixel data corresponding to the calibration scale is determined and the received image data corresponding to at least the microarray is adjusted by applying the transformation action. The adjusted image of the microarray is compared with a database of stored microarray pixel data to extract information from said image.

41 Claims, 5 Drawing Sheets

(51) Int. Cl.

| | |
|---|---|
| ***G06T 7/00*** | (2017.01) |
| ***G06F 19/00*** | (2018.01) |
| ***G06F 19/20*** | (2011.01) |
| ***H04N 1/60*** | (2006.01) |
| ***G16B 35/00*** | (2019.01) |
| ***G16B 25/00*** | (2019.01) |
| ***G16C 20/60*** | (2019.01) |
| *G16C 20/90* | (2019.01) |

(52) U.S. Cl.
CPC ..... *G06T 2207/10024* (2013.01); *G06T 2207/30072* (2013.01); *G16C 20/90* (2019.02); *H04N 1/6033* (2013.01)

(56) References Cited

U.S. PATENT DOCUMENTS

| | | | | |
|---|---|---|---|---|
| 5,891,636 | A | 4/1999 | Van Gelder et al. | |
| 6,110,426 | A | 8/2000 | Shalon et al. | |
| 6,291,170 | B1 | 9/2001 | Van Gelder et al. | |
| 6,406,849 | B1 * | 6/2002 | Dorsel et al. | 435/6.19 |
| 6,556,721 | B1 * | 4/2003 | Wang et al. | 382/282 |
| 6,718,053 | B1 * | 4/2004 | Ellis et al. | 382/128 |
| 6,785,409 | B1 * | 8/2004 | Suri | 382/128 |
| 7,085,404 | B2 * | 8/2006 | Kim et al. | 382/129 |
| 7,171,030 | B2 * | 1/2007 | Foran et al. | G06F 19/321 382/128 |
| 7,209,836 | B1 | 4/2007 | Schermer et al. | |
| 7,586,642 | B2 * | 9/2009 | Chiba | H04N 1/6033 358/1.9 |
| 8,068,988 | B2 * | 11/2011 | Gholap et al. | 702/19 |
| 8,208,710 | B2 * | 6/2012 | Weiner et al. | 382/133 |
| 8,488,863 | B2 * | 7/2013 | Boucheron | 382/133 |
| 2002/0106119 | A1 * | 8/2002 | Foran | G06F 19/321 382/133 |
| 2002/0168639 | A1 * | 11/2002 | Muraca | 435/6 |
| 2003/0012420 | A1 * | 1/2003 | Verwoerd et al. | 382/133 |
| 2003/0072476 | A1 * | 4/2003 | Kim et al. | 382/128 |
| 2003/0099973 | A1 | 5/2003 | Wang et al. | |
| 2003/0138140 | A1 * | 7/2003 | Marcelpoil et al. | 382/162 |
| 2003/0147552 | A1 * | 8/2003 | Foran et al. | 382/128 |
| 2004/0064264 | A1 | 4/2004 | Corson et al. | |
| 2004/0170325 | A1 * | 9/2004 | Eichhorn et al. | 382/205 |
| 2004/0240718 | A1 * | 12/2004 | Mori | 382/129 |
| 2005/0123181 | A1 * | 6/2005 | Freund et al. | 382/128 |
| 2005/0239114 | A1 | 10/2005 | Ryu et al. | |
| 2006/0041385 | A1 * | 2/2006 | Bauer et al. | 702/19 |
| 2006/0127946 | A1 * | 6/2006 | Montagu et al. | 435/7.1 |
| 2006/0211044 | A1 * | 9/2006 | Green | 435/7.1 |
| 2006/0222227 | A1 * | 10/2006 | Seul et al. | 382/128 |
| 2010/0111396 | A1 * | 5/2010 | Boucheron | 382/133 |
| 2010/0142850 | A1 * | 6/2010 | Weiner et al. | 382/275 |
| 2010/0208955 | A1 * | 8/2010 | Mehes et al. | 382/128 |
| 2012/0010528 | A1 * | 1/2012 | Donovan et al. | 600/567 |
| 2012/0015052 | A1 | 1/2012 | Donovan et al. | |
| 2012/0082362 | A1 * | 4/2012 | Diem et al. | 382/133 |

OTHER PUBLICATIONS

Porro Ivan et al., A Grid-based solution for management and analysis of microarrays in distributed experiments, BMC Bioinformatics, Biomed Central, vol. 8, No. suppl 1, Mar. 8, 2007.

* cited by examiner

SYSTEM AND APPARATUS FOR THE REMOTE ANALYSIS OF CHEMICAL COMPOUND MICROARRAYS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[CROSS-REFERENCE] *CROSS REFERENCE* TO RELATED APPLICATIONS

This application *is a reissue of U.S. Pat. No. 8,873,815, issued on Oct. 28, 2014, which* claims the benefit of U.S. patent application Ser. No. 61/440,748, filed Feb. 8, 2011, *each of* which is hereby incorporated by reference in its entirety.

FIELD OF THE INVENTION

The present invention relates to microarray image detection and the remote analysis of the results, as well as systems and methods in support of calibratable data capture, image processing, and data analysis.

BACKGROUND OF THE INVENTION

Screening for small molecules based on binding is of critical importance to many fields of modern medicine. Through the use of microarrays, it is possible to identify, for example, small molecules that are indicative of disease or illness. Currently, small molecule arrays (SMA), which is a maturing technology, are capable of hosting numerous reactants, proteins, and DNA samples.

High density microarrays are being used in a variety of medical and pharmaceutics practices to assist in identifying novel compounds or illness vectors. Currently, microarrays are being employed in fields such as clinical diagnostics, toxicology, genomics, drug discovery, environmental monitoring, genotyping and many other fields. A microarray is an orderly arrangement of samples containing a reactant. It provides a medium for matching known and unknown samples based on biochemical interactions and automating the process of identifying the unknowns. Microarrays available include oligonucleotide/DNA microarrays (see U.S. Pat. Nos. 6,291,170; 5,807,522 (inventors Shalon and Brown); U.S. Pat. Nos. 6,110,426; 5,716,785 and 5,891,636, (inventors Eberwine et al)). Reviewing the outcome of microarray experiments can entail viewing the arrays under UV (ultraviolet) light, as well as matching dispersion blots and patterns to know reference images. Machine and optical scanners have been developed to look at DNA chips and other expensive laboratory equipment. They include the cluster analysis of fluorescent images and other multiple pass image hybridization and compositing. (See U.S. Pat. No. 7,031,844; U.S. Patent Application Pub. 2004/0240718 and U.S. Patent Pub. 2005/0239114.)

Compound Arrays, or chemical "compound microarrays" ("CMA"), are microarrays that can provide chemical compounds with varying molecular weights immobilized on a medium. CMAs containing numerous unique chemical compounds attached to a biologically inert supporting surface provide for the identification of agents that modulate biological processes. For example, CMAs can be used to actively study the binding of proteins and enzymes or gene transcription. Proteins generally have binding sites for small molecules for important biological reasons. These molecules may act as substrates, inhibitors, activators, or even transcriptional regulators of the protein, interacting through one or more independent binding sites on the polypeptide.

CMAs are printed or deposited, as in a sequence of reservoirs for chemical compounds (a probe). These compounds are designed to react or bind with biological agents (reactant). For example, it is envisioned that CMAs could be probed so as to indicate the presence of specific protease genes and transcription enzymes that are indicative of a disease such as HIV. Thus, CMAs can be probed with an oligonucleotide probe and designed to emit phosphoresce when the reactants corresponding to reverse transcriptase and protease of polymorphic HIV-1 are found. Since these results are quickly obtainable, it is desirable to distribute more CMAs to geographical regions in need of additional medical testing apparatus.

The complexity of the hardware and analysis of the CMAs is a current barrier to the wide spread adoption of the technology in rural areas. Currently, on-site microarray analysis is difficult and expensive to undertake in areas lacking adequate and consistent access to electricity and other laboratory necessities. Furthermore, the nature of low medical service areas means that large and complex analysis apparatus are subject to extreme weather conditions and adverse treatment.

SUMMARY OF THE INVENTION

In accordance with a broad aspect of the invention, the present invention provides for a system and apparatus for the remote analysis of chemical compound microarrays. In more particular aspects, the present invention provides remote computer-mediated analysis of an image of a chemical compound microarray via remote computer servers of the type that have at least one processor, memory, and code that configures the processor to perform functions as described herein. In part, the present invention enables a medical profession, clinician, aid worker, or other member of the community to provide chemical compound microarrays to ill individuals and receive analysis of the present health state. Herein, the term patient is used to represent the subject of the microarray analysis. However, the claimed invention envisions that a user may use the remote analysis to gain information on their own medical state without the necessity of scheduling an appointment with a medical professional. Therefore, it should be understood that a user and a patient can be the same individual. It is further conceived that the present invention can be used in any location with access to a network, by untrained personal so as to test others or themselves for medical conditions. The present invention also enables, in part, the individual to access information regarding current health states via any device capable of connecting via a network to a remote database. A system and method according to the invention can be configured to enable the individual to test biological materials of a patient on a chemical compound microarray and, based on the capture of an image taken of the array and a remote analysis system, discover any pressing health concerns, or illness levels. In particular, the images can be taken by any sort of imaging still or video camera and uploaded via a wireless internet or cellphone connection. Remote diagnostic systems analyze the image and extract diagnostic image. Completed diagnostics are then returned to the patient or health care worker for consultation or discussion of treatment options.

Embodiments of the present invention seek to provide a system that simplifies the CMA process of obtaining a biological sample while at the same time allows for increased portability of the analysis mechanisms. Preferred embodiments of the present invention seek to provide a system designed to not only capture the data, but which can record optical data captured as an image from a CMA in the field. This data is then preferably transferred to a remote analysis location wherein the image is processed using the results from reactions observed in the image, and corrected for errors. Embodiments of the present invention further seek to provide a remote analysis system that can process images from any image source and can optionally calibrate the image so as to allow the proper analysis of the image.

The analysis functions are preferably hosted on-line and allow users to access them remotely, without the need to download or install any software. The advantages of this system are readily apparent. The present invention is adapted to enable a user ("medical personnel") to access the diagnostic functions by sending an image to the remote server via an e-mail, web portal, or mms text message. Through the remote system, medical data can be stored and comparisons between previous tests and reading can be made. The medical personnel can use the remote analysis to obtain more technical information regarding potential co-morbidity, complications, nutritional information, and general health guidelines depending on the test results.

The network-based remote analysis allows for a wide variety of personal devices (portable computer, desktop, PDA, smart-phone, camera phone, web camera, and so on) to access and receive the system free of quality issues resulting between different make, models and settings of various camera containing devices. Furthermore, remote access provides for less resource draw on a device, and allows simpler communication devices, such as simple picture phones to be used to record the image and receive the analysis. It is envisioned that both domestic users and foreign aid or medical workers could employ the remote analysis herein described. It is further envisioned that the present invention provides a lower cost solution to standard paper indicator tests currently on the market.

In an illustrative embodiment of the invention, medical personnel can provide a microarray that supports several compounds that, when exposed to a sample such as a biological agent containing specific reactants (e.g., protease enzymes, gram-positive polysaccharides, retinol presence), a chemical sample having a specific composition or concentration, or some other sample such as a geological sample having presence of some chemical, mineral etc, induce a change of color or change of color properties of the compound. As such, a microarray can be printed on a substrate, or embedded in a matrix or gel such that voids or spots are introduced to immobilize chemical compounds (probes). These spots are enriched with a particular probe that will bind to a selected protein or macromolecule, or other chemical (RNA, DNA, amino acid). In this manner, high-density CMAs offer the possibility of probing and reacting with several molecules in a small area The CMAs can offer a repeating pattern of probes across the surface of a substrate so as to allow a color changing spots to be easily identified for microarray specific element detection. The microarray also includes or has an associated calibration scale (for example, if not printed on or affixed to the substrate or otherwise integrated into the substrate, the calibration scale may be included in the packaging or may even be part of the packaging). Reference data on the calibration scale is preferably stored such that when an image is received including at least a portion of the calibration scale, the reference data on the calibration scale can be accessed and compared with the received image of the calibration scale. In dependence on the comparison, lighting and other environmental influences on the received image can be filtered or otherwise removed or reduced by image processing techniques. Preferably, the calibration scale is a color scale having a plurality of discrete elements (or a continuous element) changing through a range. The range may be a color spectrum or a subset of a color spectrum. In one embodiment, the range may be selected in dependence on the color change exhibited by the probes when exposed to samples. For example, if the probe changed color from red to blue then the calibration scale may also be shade or red and blue. Alternatively, the calibration scale may be independent of the color changes and/or may be selected on the expected environment of use. In selected embodiments, a plurality of calibration scales may be included on a microarray that are selected for particular environments or to accommodate differences in image acquisition devices.

In use, the microarray is exposed to a sample. After waiting for a sufficient period of time, the user/patient/medical personnel records an image of the exposed microarray, ensuring to also record the integral color calibration scale. A variety of image acquisition devices, which can be, for example, a CCD (charge coupled device), are used for detecting binding patterns. The medical personnel can then send this image to the remote analysis application via e-mail, text message, file transfer or other electronic data transfer. The data analysis application is configured to execute within a processor so as to inspect the image and locate (identify) calibration markers that are associated with the substrate that supports the microarray(s). The pixels representing the calibration markers are compared to a set of reference pixels in a database or in a memory store that correspond to those specific markers. The image analysis application alters the image (or at least the data values or at least a subset of the pixels) so as to calibrate the pixels of the image to correlate to the properties of the reference pixels. The image application is further configured to inspect (analyze) the pixels in the image, and identify those colors within a gradient range of the calibrated pixels. The image application then compares the pixel values with values stored within the database or the memory store. The stored values can correspond to a particular illness, while the intensity of the colors of the image can correspond to the severity of the infection, deficiency, or status.

According to an aspect of the present invention, there is provided a computer implemented method for the remote analysis of a chemical compound microarray supported on a substrate, the remote analysis executed as an application residing on a computing device, the computing device having a processor and a storage medium, and the remote analysis application having one or more software modules stored on the storage medium and executed in the processor, the method comprising:

receiving pixel image data from a remote location including image data that depicts (a) a calibration scale associated with the substrate and (b) the microarray;

determining a transformation action of said pixel data corresponding to the calibration scale using a calibration module;

adjusting the received image data corresponding to at least the microarray by applying the transformation action using an adjustment module;

comparing the adjusted image of the microarray with a database of stored microarray pixel data to extract information from said image using an analysis module;

outputting the information to a remote device.

The calibration scale may comprise a color scale, at least a portion of the microarray may be arranged to exhibit a color change upon being exposed to a sample having predetermined properties, the method further comprising storing reference data on the calibration scale, the step of determining the transformation action including determining a transformation action to transform at least a subset of the image data depicting the calibration scale to values corresponding to a corresponding subset of the reference data.

According to another aspect of the present invention, there is provided a remote microarray analysis system configured to remotely analyze a chemical compound microarray supported on a substrate, comprising:

a data communication module configured to receive pixel image data from a remote location including image data that depicts (a) a calibration scale associated with the substrate and (b) the microarray;

a calibration module configured to determine a transformation action of said pixel data corresponding to the calibration scale using a calibration module;

an adjustment module configured to adjust the received image data corresponding to at least the microarray by applying the transformation action using an adjustment module;

an analysis module configured to compare the adjusted image of the microarray with a database of stored microarray pixel data to extract information from said image using an analysis module;

a data output module configured to output the information to a remote device.

The calibration scale may comprise a color scale and at least a portion of the microarray may be arranged to exhibit a color change upon being exposed to a sample having predetermined properties, the system further comprising a memory encoding data on the calibration scale, wherein the calibration module is configured to determine the transformation action by accessing the reference data in the memory and determining a transformation action to transform at least a subset of the image data depicting the calibration scale to values corresponding to a corresponding subset of the reference data.

The calibration module may be configured to operate as a discrete series of sub-modules configured to check at least a portion of the pixel data corresponding to the calibration scale against the set of reference pixels that comprises one or more parameters selected from the group consisting essentially of: luminosity, a shadow, a highlight and a color temperature, and determining the transformation action.

The adjustment module may be configured to operate as a discrete series of sub-modules comprising adjusting the pixel value levels of one or more parameters selected from the group consisting essentially of a luminosity, a shadow, a highlight and a color temperature.

The adjustment module may further comprise an image correction module configured to operate as a series of discrete sub-modules for identifying all pixels that share one or more parameters selected from the group consisting essentially of a luminosity, a shadow, a highlight and a color temperature and adjusting said pixels in a similar manner.

The analysis module may be configured to operate as a series of discrete sub-modules configured to check at least a portion of the pixel data corresponding to the image and comparing said pixels to a database of stored parameters, where stored parameters correspond to a specific biological analysis.

The calibration scale may be supported on the substrate.

The image data may be sent via the internet.

The remote device may be configured to send and receive image data.

The database may be integral to the computing device.

The remote device may be further configured to include an image capture device.

According to another aspect of the present invention, there is provided an apparatus for remotely analyzing a plurality of microarray images, the apparatus comprising:

a support comprising a chemical compound microarray;

a calibration scale associated with at least one of the support and the microarray;

an image recording device configured to record an image of the chemical compound microarray and the calibration scale after usage of the microarray;

a data communication device configured to transmit the image via a network;

a network connected image analysis device configured to receive the image and analyze the data contained therein.

The chemical compound microarray may further comprise an array of immobile target compounds.

The introduction of an analyte compound may initiate a color change of the target compound.

The color change of the target compound may be within a gradient spectrum of a reference color present on the calibration scale.

The color of the target compound relative to the gradient may be correlated to the amount of said analyte.

The image analysis device may be a computer having a processor and a storage device.

The data communication device may be further configured to transmit images via the internet.

The images may be transmitted via wireless protocol.

The calibration scale may be supported on the substrate.

While it is envisioned that the present invention will be of great assistance to identifying illness in places located far from advanced medical facilities, those skilled in the art would recognize that nothing in the foregoing embodiments prevents those with access to advance facilities from using the present invention to supplement current diagnostic testing regimes.

These and other aspects, features and advantages of the invention can be appreciated from the accompanying description of certain embodiments of the invention and the associated drawing figures.

BRIEF DESCRIPTION OF THE DRAWING FIGURES

DESCRIPTION OF CERTAIN EMBODIMENTS OF THE INVENTION

By way of example only and for the purpose of overview and introduction, embodiments of the present invention are described below which concern a system and apparatus for the remote analysis of microarrays. The system is directed to assisting medical professionals to obtain rapid analysis of biological and/or chemical specimens and to rapidly diagnose medical conditions in remote locations. The system is further directed to a remote analyses application that corrects for differences in equipment and environmental conditions. Through the remote analysis system, medical professionals are able to receive information regarding the heath status of a patient and properly proscribe treatment based on a number of biological factors and tests reviewed while not having physical access to sophisticated medical and array diagnostic tools.

Figure 1:
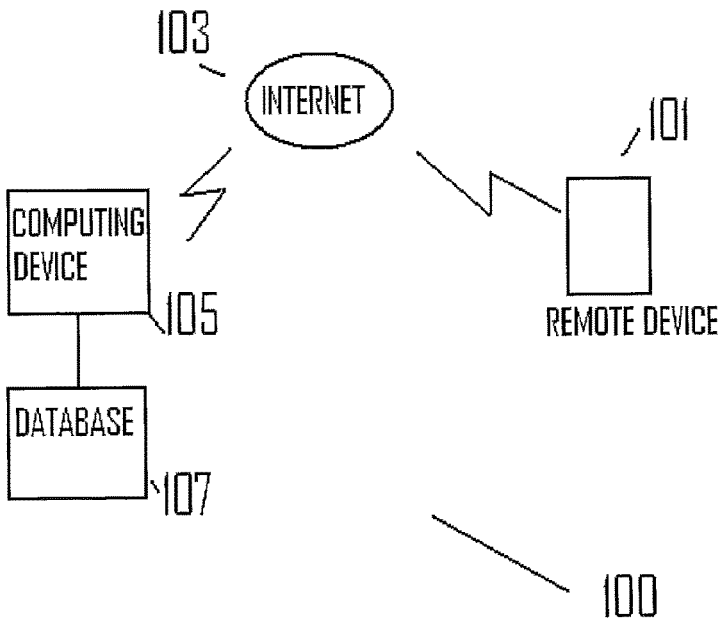
FIG. 1 is a schematic block diagram of a system according to one embodiment of the invention, highlighting certain interconnected modules thereof.

As seen in FIG. 1, the remote microarray analysis system comprises a system 100. The system 100 uses a bidirectional data communications network, such as the interne 103, to establish a communication link that connects a remote device 101 to a computing device 105. The computing device 103 is configured to connect to the remote device (101) and receive image data corresponding to a particular chemical microarray. The computing device 105 can utilize commonly used network programming platforms and databases 107. The computing device 103 can connect to networks and databases using commonly understood programming interfaces and interface modules 111, e.g., Media Server Pro, Java, Mysql, Apache, Ruby on Rails, and other similar application programming interfaces and database management solutions. It will be appreciated that the remote microarray analysis system of preferred embodiments of the present invention offers broad adaptability to user configurations, multiple user inputs, and hardware configurations.

The remote microarray analysis system may be accessed, for example, by way of a web portal, e-mail, or text message. The computing device is capable of and configured to receive industry standard telecommunications for data transfer. Furthermore, the computing system is capable of parsing telephone, e-mail, and other header data so as to enable a return message to be sent to a user using conventional protocols as is commonly known (e.g., using the Automatic Number Identification (ANI) in a telephone call set-up, or sender address information in an email). The remote microarray can be connected to in a conventional manner, such as by using a web browser program such as Mozilla's Firefox. The web portal offers the ability to transmit data from non-networked sources such as digital cameras, web camera, and digital tape feed.

The remote microarray analysis system provides the user with access to diagnostic functions associated with analyzing a particular microarray. This enables a user to identify specific medical issues relating to health and general well-being of a subject, without the need to transport perishable biological samples to a stationary analysis machine The system accomplishes this by executing a series of software modules that cooperate to analyze the image data received remotely.

Figure 2:
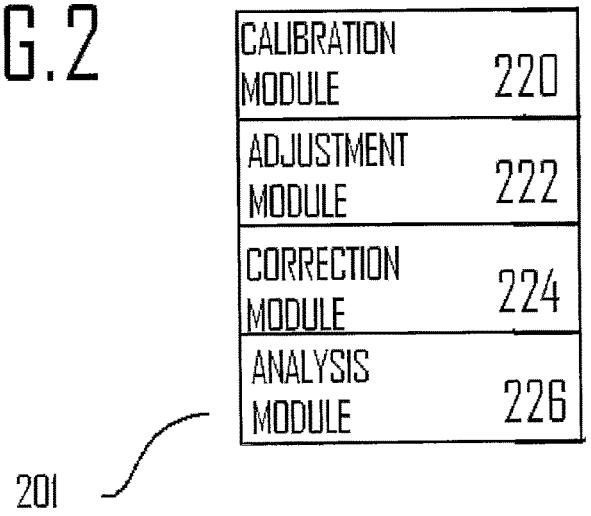
FIG. 2 is a set of modules that cooperate to provide functionality to a user through a server such as is a component of the system of FIG. 1.

More specifically, as shown in FIG. 2, a set of modules cooperate with one another to provide a diagnosis of various medical conditions determined by the microarray. Thus, in one exemplary embodiment, there is a calibration module 220, an adjustment module 222, a correction module 224 (which, as will be appreciated from the description below, can be incorporated as part of the functionality of the adjustment module), and an analysis module 226. Each of these modules can comprise hardware, firmware, code executing in a processor, or some combination thereof, that configures a machine such as the computing device 105 to implement the functionality described herein. The functionality of these modules can be combined or further separated, as understood by persons of ordinary skill in the art, in analogous implementations of embodiments of the invention.

With further reference to FIG. 2, the calibration module 220 includes instructions that, when executed, cause reviewing of the received image data and locating calibration pixel markers located in or proximate to the image. For instance, the calibration pixel markers can be supported on the same substrate as the microarray and can be viewable from the same side of the support as the microarray. The calibration module compares these calibration pixels to reference pixels stored in the database or in a memory store (more generally, the database and the memory store are collectively referred to as the database) that correspond to the particular make and model of the microarray in question. The calibration module then identifies the adjustments or transformations needed to the change the parameters of the calibration pixels in view of the appropriate set of reference pixels for that CMA. These functions can be implemented as discrete sub-modules providing the ability to reference, by way of example and not limitation, the color temperature, luminosity, highlight, hues and other parameters of one or more of the calibration pixels, and compare those parameters to a reference pixel. As one example, as would be apparent to a person of ordinary skill in the art, the pixels can be mapped as an array of values and then a transformation matrix can be determined as a matrix of values that, when multiplied by calibration pixel markers within the image data, result in a result matrix of values that correspond to the values of the reference pixels for that CMA.

The adjustment module 222 includes instructions for interpreting the difference between the parameter values of the calibration pixels and the reference pixels. The adjustment module then adjusts or transforms the parameters of the calibration pixels so that they equal or closely approximate the parameters of the reference pixels.

The adjustment function of the adjustment module can be implemented as discrete sub-modules to provide functions such as, by way of example and not limitation, filtering, color correction, hue correction, saturation level alteration and chromatic aberration alterations. The adjustment module can alter all the calibration pixels in relation to the reference pixels. Conversely, the adjustment module can alter specific pixels in relation to the reference pixel.

The correction module 224 includes instructions for correcting the remaining pixels of the image so as to calibrate the total image for analysis. The correction module receives data corresponding to the parameter levels necessary to alter each pixel so as to calibrate the entire image or a selected portion of the image. The correction module can be implemented as discrete sub-modules configured to provide the specific parameters necessary to correct, again by way of example and not limitation, the color, tones, hue and saturation of the entire image relative to the reference pixels.

In an alternative arrangement, the functions of the correction module 224 are incorporated into the adjustment module 222 such that the pixels representing the microarray are adjusted or transformed contemporaneously with the calibration pixels. In a further arrangement, the correction module, when incorporated into the adjustment module only adjusts or alters those pixels relating to the microarray and not the image calibration pixels.

Analysis module 226 includes instructions for analyzing the image of the microarray and identifying the color and intensity of pixels throughout the image of the microarray. The analysis module compares each colored pixel and its intensity against data stored in the database. The data may be in the form of a look up table of colors. The analysis module correlates the color and intensity for a specific microarray reaction site and determines if a given medical condition is present in the sample in dependence on associations in the database (or in some other system) between the color and/or intensity and prior results from using the respective probe for the condition. A listing of all the present medical conditions and the severity of each, for a given microarray, is stored for transmission. The analysis module can be implemented as discrete sub-modules configured to provide the specific analysis functions for interpreting the color and intensity of a given reaction site, looking up in a data base the specific ailment or condition correlated to that site, comprising a list of aliments and their severity, storing the list for transmission to a hand-held device.

Figure 3:
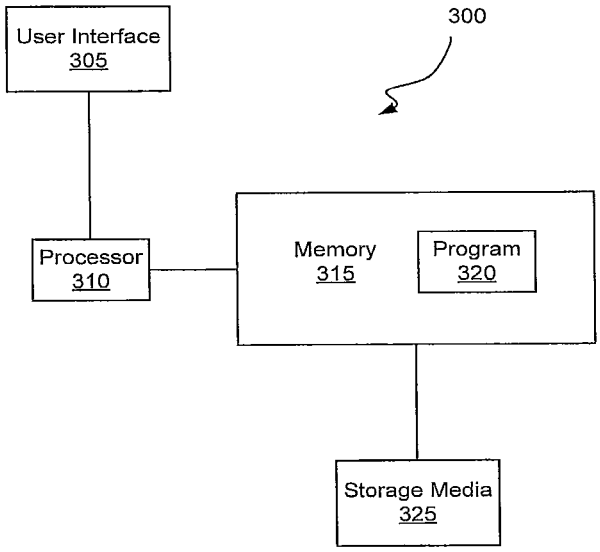
FIG. 3 is an illustrative diagram of the system designed to implement at least selected steps of the method of an embodiment of the claimed invention.

As shown in FIG. 3, a personal device 300 such as a portable computer, desktop, PDA, smart-phone, camera phone, web camera, and so on is configured for employment of at least selected steps of the method as described above. The device 300 includes a user interface 305, a processor 310, a memory 315 and a camera 504 (described below). Device 300 may comprise one or more of any number of commercial devices or systems that are capable of capturing optical data through a lens and transmitting an image file that includes the captured data. As one non-limiting example, a smartphone that executes the Android operating system by Google, Inc, and which has a camera for capturing images is a suitable device 300. Although the device 300 is represented herein as a single device, it is not limited to such, but instead can comprise a camera coupled to another system that enables image transfer over a network to the computing device 105 of FIG. 1.

Memory 315 is a memory for storing data and instructions suitable for controlling the operation of processor 310. An implementation of memory 315 would include a random access memory (RAM), a hard drive and a read only memory (ROM). One of the components stored in memory 315 is a program 320.

Program 320 includes instructions for controlling processor 310 to execute method 100. Program 320 may be implemented as a single module or as a plurality of modules that operate in cooperation with one another. Program 320 is contemplated as representing a software embodiment of the modules that implement the functionality and methodology described herein.

User interface 305 includes an input device, such as a keyboard, touch screen, tablet, or speech recognition subsystem, for enabling a user to communicate information and command selections to processor 310. User interface 305 also includes an output device such as a display or a printer. In the case of a touch screen, the input and output functions are provided by the same structure. A cursor control such as directional keys, a mouse, track-ball, or joy stick, can be employed to enable the user to manipulate a cursor on the display for communicating additional information and command selections to processor 310, in embodiments in which the display is not a touch screen.

While program 320 is indicated as already loaded into memory 315, it may be configured on a storage media 325 for subsequent loading into memory 315. Storage media 325 can be any conventional storage media such as a magnetic tape, an optical storage media, a compact disc, or a floppy disc. Alternatively, storage media 325 can be a random access memory, or other type of electronic storage, located on a remote storage system.

Figure 4A:
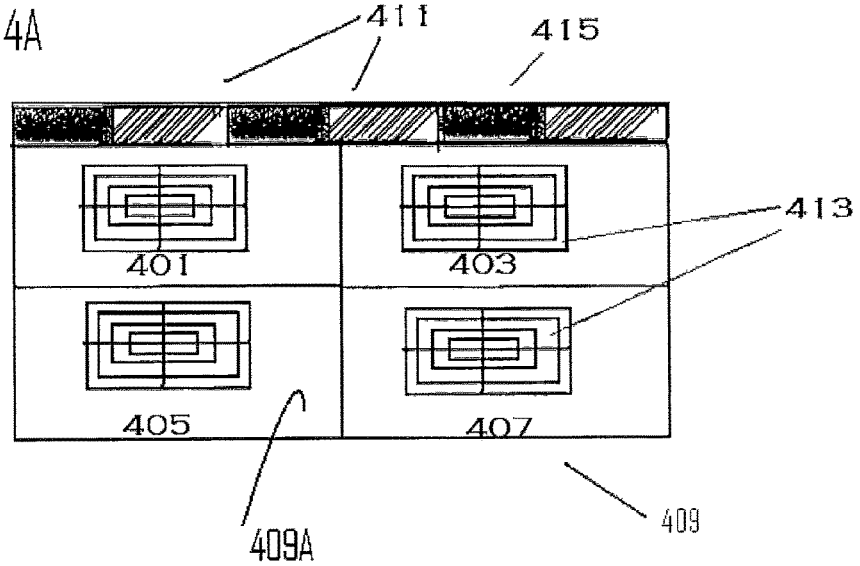
FIG. 4A is an illustrative diagram of a top surface of a microarray that can be used in accordance with the invention.
Figure 4B:
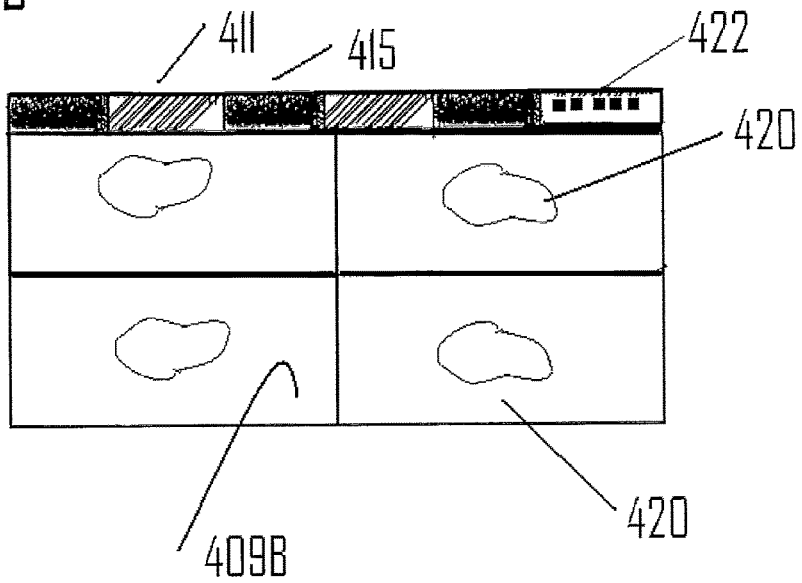
FIG. 4B is an illustrative diagram of a bottom surface of the microarray of FIG. 4A.

Referring now to the diagram of FIGS. 4A-4B, a microarray is depicted showing the various elements thereof that may be used in the operation of the claimed system and apparatus, The microarray 409 is divided into two discrete sections. The main section is itself divided into several smaller sections each containing an array of reaction sites containing probe chemical compounds 401-407. The microarray is designed to provide an array of reaction sites 413 wherein each of a plurality of probe sites is dedicated to (that is supports) one probe compound. In this way, all the probe compounds of a given array are ensured to be exposed to a biological and/or chemical sample. The ancillary section is a calibration scale 411. The calibration scale is preferably integral to the micro array and is designed to indicate via a clearly visible marker, its orientation. The calibration scale also can include a series of colored strips 415 corresponding to the color gradients of all of the included reactant colors possible for a given microarray. In this way, in one embodiment, a spectrum (from white to maximum intensity) of each specific reactant color is provided on the substrate or matrix of the microarray. In an alternative embodiment, the calibration scale has a selected image or discrete color markers that is/are provided to the calibration module 220 (described above).

In a preferred embodiment, a patient interacts with the microarray 409 by contacting one of the two broad surfaces presented. In FIG. 4A, a top surface 409a is illustrated. A camera is used to capture an image of the top surface 409a of the microarray 409 as well as the calibration scale 411 which is proximate to the reaction sites 413. In certain embodiments, the patient contacts the top surface 409A and the camera 504 instead captures an image from an opposite, rear surface 409B. The rear surface 409B can present a reaction 420 between the biological sample and the probe chemical compounds 401-407 at the respective reaction sites 413 in proximity to a calibration scale 411 included on the rear surface. When a patient puts a biological or chemical sample on the probe (e.g., blood, saliva, urine, or some other sample as may be appropriate for a given probe), the reactant color change is such that a color contrast arises that can be captured by the camera 504 when held a short distance away from the surface of the array. In an alternative arrangement, a calibration scale that is correlated closely with the reference data in the database 107 can be provided separate from the microarray 409 and interposed into the camera's field of view when an image is captured from the microarray 409, but this is less preferred as it can result in contamination of one patient's sample when brought into contact with that patient's sample after contacting another patient's sample.

In still another embodiment, as depicted in FIG. 4B, the area designated 409B can present a unique array model and make marker 422 that is unique to that particular array, so as to identify a patient or test conducted. This can be represented as a serial number, bar code, q-code, or other pictographic or alphanumeric unique identifier. As such, The image need not be captured in a specific orientation or positioning. The device is configured to differentiate between the microarray and the integral calibration portions of the substrate, such that various imaging orientations are possible.

It is envisioned that the microarray can be printed on a substrate such as paper, plastic, thin metallic films, or composite materials. It is envisioned that the probe molecules could be doped, sprayed, dry immobilized or otherwise secured to a piece of testing paper, such as litmus paper. Furthermore, it is envisioned that the printing process or doping process that forms the array is capable of depositing several different probe chemicals within the various probe spots within a single array. Additionally, it is envisioned that multiple arrays can be printed on a single paper or wafer substrate.

In one embodiment, the microarray employs reactants within the surface of the microarray to bind to particular macromolecules to initiate the color changing function. For example it is envisioned, and is no way limiting that the probe for a particular site for a microarray for a biological sample contains soluble glycolic enzymes such as Glutamate dehydrogenase. In this way, a binding site between the enzyme and the biological sample can be made to change color upon the binding of the immunoglobulins to the reactant (such as a buffer). It is preferable to allow a repeating pattern of binding sites containing a few specific probe compounds. For example, a series of antigens and metabolic products that co-indicate infection with Plasmodium falciparum (malaria) could be located within a single may. In this way, all the probe compounds of a given array could be used to both indicate the strain of a malarial infection by preparing IgG compounds and oxidoreductase compounds so that binding of the antibody or lack thereof to a signal reagent confers information regarding strain of parasite and the level of infection. Additionally, multiple disease states can be tested on a microarray. By way of non-limiting example, the above malarial reagents and antibodies could be included on array 401, while a separate array for HIV screening can be placed on another array (e.g. 403-407). The biological specimen would be applied in a sequence to the center of each array. Depending on the testing undertaken, it might be necessary to obtain a fresh sample for each screening array. The specimen migrates through the array and combines with the signal reagent. A positive reaction results in a visual color indicator on the array HIV antigen has been applied. Some arrays could apply HIV-1 and HIV-2 antigens in different locations and allow differentiation of antibodies to these two viruses. It is envisioned that the reagent, chemical compound or signal compound require no additional equipment or refrigeration, and test results can be obtained in several minutes or less. It is also envisioned that the arrays can use samples obtained from whole blood, serum, or plasma, and some combination of finger-stick blood specimens and other sampling means.

In another embodiment of the present invention, it is envisioned that sporting events would employ the present invention for spot checks regarding banned performance enhancing agents and medicines. This could be accomplished by acquiring samples, for example urine or saliva, from a number of contestants and using the present invention to remotely test those samples for a variety of substances. It is further envisioned that general health states (e.g. cholesterol levels, blood glucose levels, vitamin levels) could be obtained by a microarray designed to engage reactants with various indicators of health and wellbeing. For example, by way of non limiting examples, the present invention could be distributed at health and fitness facilities so that individuals can independently track their metabolic states during the course of a fitness regime.

Figure 5:
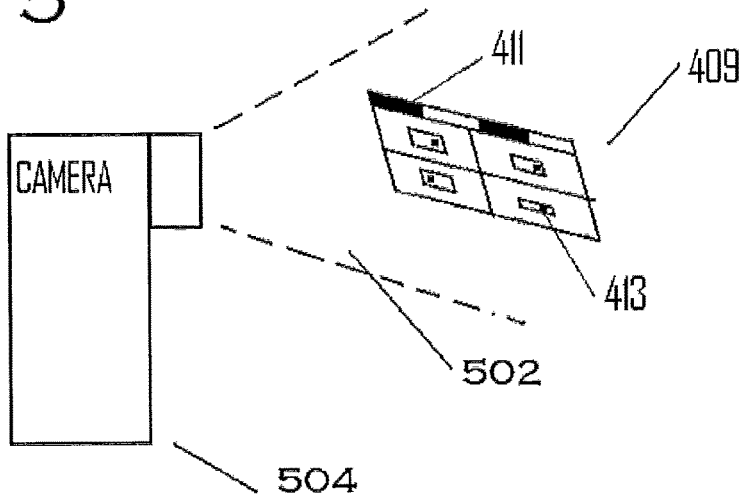
FIG. 5 is a diagram illustrating the relationship between the microarray and an image recording device that can be used to implement one embodiment of the invention.

As seen with respect to FIG. 5, a user such as a health care provider can capture an image, with an image recording device or camera 504, of the microarray 409 so that both the reaction sites 413 and the calibration scale 411 are within the field of view 502. The camera 504 to be employed for this purpose should be of sufficient capability as to be able to differentiate between the different reactant sites of the microarray 409 at a distance necessary to record the sites and their corresponding calibration scale (and preferably the entire microarray 409, including the calibration scale 411) In use, a user secures a biological sample from a patient, e.g., a blood sample, and applies it to the microarray. The user then captures an image (e.g., a photograph) of the microarray 501 while capturing the calibration scale in the image being taken. This image is then uploaded to the remote analysis system 105 for analysis. In one arrangement of the apparatus, the remote analysis system 105 analyzes the calibration scale 411 included in the transferred image and calibrates the color and tones of the image so that they match a stored reference image using the functionality of the calibration module 220, the adjustment module 222 and the correction module 224. Using the information regarding the corrected and calibrated image, the analysis system can then locate the proper color-changed reaction sites that indicate the presence of illness or disease using the functionality of the analysis module 226. The remote analysis system then compiles a listing of all the medical states indicated by the microarray and transmits the list in a manner designed to ensure receipt be the sender of the image. For example, if the image is transmitted to the remote analysis system via e-mail, that a return e-mail is sent to the sending address indicating the medical states diagnosed by the microarray and remote analysis.

Figure 6:
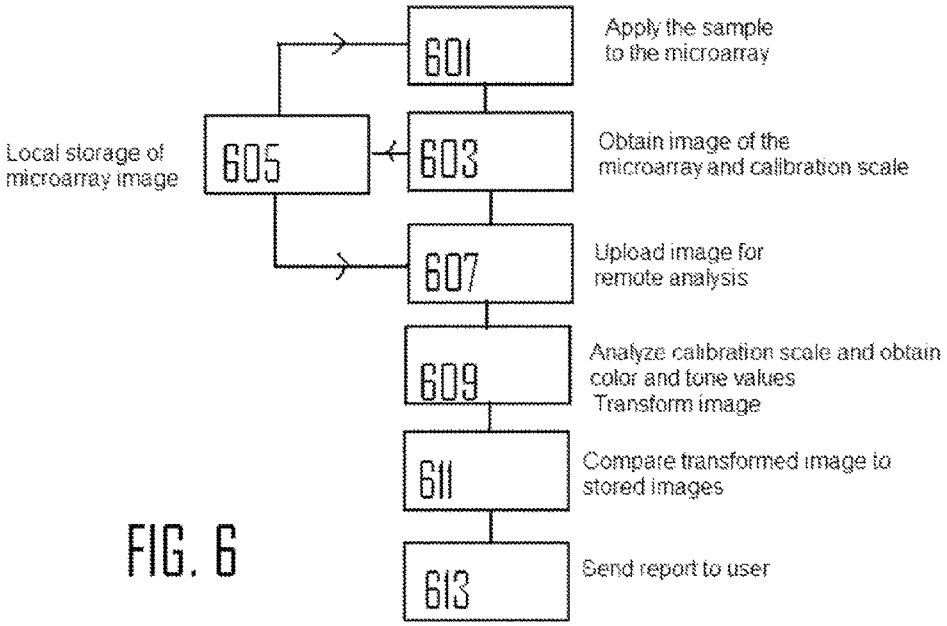
FIG. 6 is a flow chart illustrating the necessary steps taken in accordance with an embodiment of the invention.

In further aspects of the invention, the analysis system executing at or as the computing device 105 can utilize additional data such as local geography (including GPS data from the device 101 connected to the camera 504 that captured the image) to compile medical data useful for statistical analysis. In this regard, the initial image transmission can be done using a unique or specific identifier that does not identify to the system 105 any personal data of the patient. Thus, for instance, the health care provider (HCP) sending the image file to the system 105 can have an account and each time that a message is sent from that HCP, a serial number can be assigned to the communication and combined with that HCP's identification rather than an identification of the patient himself or herself As seen in FIG. 6, a flow chart is provided giving indication of the proposed steps of the claimed invention are illustrated. The depicted flow chart is of one embodiment of the present invention. Those skilled in the art would understand that modifications and alterations to the disclosed plan are readily apparent. It is understood that a medical professional would secure a biological sample from a subject. For example the medical professional could obtain a blood sample, tissue sample, fluid sample or other biological sample in need of testing. This sample is then applied to the microarray 601. Once the probe chemicals of the microarray have had sufficient time to react with the biological sample, the medical professional or user would then photograph the microarray 603. The medical professional or user preferably ensures that the image includes both the reaction sites, as well as sufficient numbers of the calibration markers. Once the image is taken, the medical professional or user can the store the image locally 605, or immediately upload the image to the remote analysis system 607. The medical professional or user can record and store multiple images relating to several different arrays. If the medical professional or user has a large amount of images, then they can be batch uploaded to the remote system for processing. The remote analysis system analyzes the calibration scale and calibrates the color and tones of the image so that they match a reference image stored on the remote analysis system 609. Using the information regarding the corrected and calibrated image, the analysis system can then locate the proper color-changed reaction sites that indicate the presence of illness or disease 611. The remote analysis system then compiles a listing of all the medical states indicated by the microarray and transmits the list in a manner designed to ensure receipt by the sender of the image 613. For example, it is envisioned that if the image is transmitted to the remote analysis system via e-mail, that a return e-mail is sent to the sending address, indicating the medical states diagnosed by the microarray and remote analysis.

The remote analysis system may include a camera for use in obtaining reference calibration scale imagery in controlled (known) conditions prior to sending microarrays out into the field for use. In this manner, the degree of accuracy of manufactured/printed calibration scales is reduced as reference data can be obtained on a case by case basis.

It should be understood that various combination, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

I claim:

1. A computer implemented method for the remote analysis of a *respective* chemical compound microarray supported on a substrate, the remote analysis executed as an application residing on a computing device, the computing device having a processor and a storage medium, and the remote analysis application having one or more software modules stored on the storage medium and executed in the processor, the method comprising:

receiving pixel image data from a remote location, including image data that depicts within the field of view of an image acquisition device configured to obtain an image, (a) a calibration scale associated with the substrate wherein the calibration scale includes a color scale having a plurality of color elements, each color element having a known color value *that corresponds with the respective chemical compound microarray* and (b) the *respective chemical compound* microarray;

evaluating at least one color value corresponding to at least one image pixel wherein the at least one image pixel corresponds to a location in the image depicting at least one color element of the color scale;

determining a transformation action of [said] *the* pixel data corresponding to the color scale using a calibration module so as to match at least the color and hue value of the at least one image pixel with the *i*) known color and hue value of the corresponding color element *for the respective chemical compound microarray*;

adjusting the received image data corresponding to at least the *respective chemical compound* microarray by applying the transformation action using an adjustment module;

comparing the adjusted image of the microarray with a database of stored microarray pixel data to extract information from said image using an analysis module; *and* outputting the information to a remote device.

2. The method of claim 1, wherein at least a portion of the microarray is configured to exhibit a color change upon being exposed to a sample having predetermined properties, the method further comprising:

storing reference data on the calibration scale, the step of determining the transformation action including determining a transformation action to transform at least a subset of the image data depicting the calibration scale to values corresponding to a corresponding subset of the reference data.

3. A remote microarray analysis system configured to remotely analyze a *respective* chemical compound microarray supported on a substrate, comprising:

a data communication module configured to receive pixel image data from a remote location including pixel image data that depicts (a) a calibration scale associated with the substrate wherein the calibration scale includes a color scale having a plurality of color elements, each color element having a known color value *that corresponds with the respective chemical compound microarray* and (b) the *respective chemical compound* microarray;

an evaluation module configured to evaluate at least one color value corresponding to at least one image pixel wherein the at least one image pixel corresponds to a location in the image depicting at least one color element of the color scale;

a calibration module configured to determine a transformation action of [said] *the* pixel data corresponding to the calibration scale using a calibration module so as to match at least the color and hue value of the pixel data to the known color values of the corresponding color scale;

an adjustment module configured to adjust the received pixel image data corresponding to at least the *respective chemical compound* microarray by applying the transformation action using an adjustment module;

an analysis module configured to compare the adjusted pixel image data of the microarray with a database of stored microarray pixel data to extract information from the adjusted pixel image data using an analysis module; *and* a data output module configured to output the information to a remote device.

4. The remote microarray analysis system of claim 3, wherein at least a portion of the microarray and calibration scale are arranged to exhibit a color change upon being exposed to a sample having predetermined properties, the system further comprising a memory encoding data on the calibration scale, wherein the calibration module is configured to determine the transformation action by accessing a reference data in the memory and determining a transformation action to transform at least a subset of the image data depicting the calibration scale to values corresponding to a corresponding subset of the reference data.

5. The remote microarray analysis system of claim 3, wherein the calibration module is configured to operate as a discrete series of sub-modules configured to check at least a portion of the pixel data corresponding to the calibration scale against a set of reference pixels that comprises one or more parameters selected from the group consisting essentially of: luminosity, a shadow, a highlight and a color temperature, and determining the transformation action.

6. The remote microarray analysis system of claim 3, wherein the adjustment module configured to operate as a discrete series of sub-modules comprising adjusting the pixel value levels of one or more parameters selected from the group consisting essentially of a luminosity parameter, a shadow parameter, a highlight parameter and a color temperature parameter.

7. The remote microarray analysis system of claim 3, wherein the adjustment module further comprises an image correction module configured to operate as a series of discrete sub-modules for identifying all pixels that share one or more parameters selected from the group consisting essentially of a luminosity parameter, a shadow parameter, a highlight parameter and a color temperature parameter; and adjusting said pixels in a similar manner.

8. The remote microarray analysis system of claim 3, wherein the analysis module is configured to operate as a series of discrete sub-modules configured to check at least a portion of the pixel data corresponding to the image and comparing said pixels to a database of stored parameters, where stored parameters correspond to a specific biological analysis.

9. The remote microarray analysis system of claim 3, wherein the calibration scale is supported on the substrate.

10. The remote microarray analysis system of claim 3, wherein the image data is sent via the internet.

11. The remote microarray analysis system of claim 3, wherein the remote device is configured to send and receive image data.

12. The remote microarray analysis system of claim 3, wherein the database is integral to the analysis module.

13. The microarray analysis system of claim 3, wherein the remote device is further configured to include an image capture device.

14. An apparatus for remotely analyzing a plurality of microarray images, the apparatus comprising:

a support comprising a *respective* chemical compound microarray;

a calibration scale associated with at least one of the support and the chemical compound microarray; the calibration scale including a color scale having a plurality of color elements, each color element having a known color value *that corresponds with the respective chemical compound microarray*;

an image recording device configured to record an image of the *respective* chemical compound microarray and the calibration scale after usage of the microarray;

a data communication device configured to transmit the image of the chemical compound microarray via a network; *and* a network connected image analysis device configured to receive the image of the *respective* chemical compound microarray, evaluate at least one color value corresponding to at least one image pixel wherein the at least one image pixel corresponds to a location in the image depicting at least one color element of the color scale, determine a transformation action of [said] *the* pixel data corresponding to the color scale so as to match at least the color and hue value of the at least one image pixel with the known color and hue value of the corresponding color element *for the respective chemical compound microarray* and analyze the data contained therein.

15. The apparatus for remotely analyzing microarray images of claim 14, wherein the chemical compound microarray further comprises an array of immobile target compounds.

16. The apparatus for remotely analyzing microarray images of claim 15, wherein the introduction of an analyte compound initiates a color change of the target compound.

17. The apparatus for remotely analyzing microarray images of claim 16, wherein the color change of the target compound is within a gradient spectrum of a reference color present on the calibration scale.

18. The apparatus for remotely analyzing microarray images of claim 17, wherein the color of the target compound relative to the gradient is correlated to the amount of said analyte.

19. The apparatus for remotely analyzing microarray images of claim 14, wherein the image analysis device is a computer having a processor and a storage device.

20. The apparatus for remotely analyzing microarray images of claim 14, wherein the data communication device is further configured to transmit images via the internet.

21. The apparatus for remotely analyzing microarray images of claim 20, wherein the images are transmitted via wireless protocol.

22. The apparatus for remotely analyzing microarray images of claim 14, wherein the calibration scale is supported on the support.

*23. A computer implemented method for analysis of a respective chemical compound microarray supported on a substrate, the analysis executed as an application residing on a computing device and being output to a remote device, the computing device having a processor and a storage medium and a camera, and the analysis application having one or more software modules stored on the storage medium and executed in the processor, the method comprising:*

*capturing, by the camera, an image comprising image pixels that depicts within a field of view of the camera: (a) a calibration scale associated with the substrate, wherein the calibration scale includes a color scale having a plurality of color elements, each color element having a known color value that corresponds with the respective chemical compound microarray; and (b) the respective chemical compound microarray;*

*evaluating, using an evaluation module executed by the processor, at least one color value corresponding to at least one of the captured image pixels, wherein the at least one of the captured image pixels corresponds to a location in the captured image depicting at least one color element of the color scale;*

*determining, using a calibration module executed by the processor, a transformation action of said captured image pixels that correspond to the color scale, so as to match at least a color value of the at least one of the captured image pixels with the known color value of the corresponding color element for the respective chemical compound microarray;*

*adjusting, using an adjustment module executed by the processor, the captured image pixels corresponding to at least the microarray by applying the transformation action, to provide an adjusted image of the microarray;*

*comparing, using an analysis module executed by the processor, the adjusted image of the microarray with a*

*database of stored microarray pixel data to extract information from said adjusted image of the microarray; and*

*outputting the extracted information to the remote device.*

*24. The method of claim 23, wherein at least a portion of the microarray is configured to exhibit a color change upon being exposed to a sample having predetermined properties;*

*further wherein the calibration scale is configured to store reference data; and*

*still further wherein adjusting the captured image pixels using the transformation action includes transforming at least a subset of the captured image pixels that depict the calibration scale to values corresponding to a respective subset of the stored reference data.*

*25. A microarray analysis system configured to analyze a respective chemical compound microarray supported on a substrate, comprising:*

*a computing device configured with a processor, a camera, and a data communications module;*

*an image capture module that captures, via the camera, an image comprising image pixels that depicts (a) a calibration scale associated with the substrate wherein the calibration scale includes a color scale having a plurality of color elements, each color element having a known color value that corresponds with the respective chemical compound microarray and (b) the respective chemical compound microarray;*

*an evaluation module configured to evaluate at least one color value corresponding to at least one of the captured image pixels, wherein the at least one of the image pixels corresponds to a location in the image depicting at least one color element of the color scale;*

*a calibration module configured to determine a transformation action of the captured image pixels corresponding to the calibration scale so as to match at least a color value of the at least one of the image pixels to the known color values of the corresponding color scale for the respective chemical compound microarray;*

*an adjustment module configured to adjust the captured image pixels corresponding to at least the microarray by applying the transformation action;*

*an analysis module configured to compare the adjusted image pixels that correspond to at least the respective chemical compound microarray with a database of stored microarray pixel data to extract information from the adjusted image pixels; and*

*a data output module configured to output the information to a remote device.*

*26. The microarray analysis system of claim 25,*

*wherein at least a portion of the microarray and calibration scale are arranged to exhibit a color change upon being exposed to a sample having predetermined properties, the system further comprising:*

*further wherein the calibration scale encodes data thereon, and*

*still further wherein the calibration module is configured to determine the transformation action by accessing reference data in the encoded data and transforming at least a subset of the image pixels depicting the calibration scale to values corresponding to a corresponding subset of the reference data.*

*27. The microarray analysis system of claim 25, wherein the calibration module is configured to operate as a discrete series of sub-modules configured to check at least a portion of the image pixels corresponding to the calibration scale against a set of reference pixels that comprises one or more parameters selected from the group consisting of: luminosity, shadow, highlight and color temperature, and to determine the transformation action as a function of the one or more parameters.*

*28. The microarray analysis system of claim 25, wherein the adjustment module is configured to operate as a discrete series of sub-modules configured to adjust pixel value levels of one or more parameters selected from the group consisting of: a luminosity parameter, a shadow parameter, a highlight parameter and a color temperature parameter.*

*29. The microarray analysis system of claim 25, wherein the adjustment module comprises an image correction module, wherein the image correction module is configured to operate as a series of discrete sub-modules for identifying image pixels that share one or more parameters selected from the group consisting of: a luminosity parameter, a shadow parameter, a highlight parameter and a color temperature parameter; and for adjusting the identified image pixels as a function of the one or more parameters.*

*30. The microarray analysis system of claim 25, wherein the analysis module is configured to operate as a series of discrete sub-modules configured to check at least a portion of the image pixels corresponding to the microarray and comparing the portion of the image pixels to a database of stored parameters that correspond to a specific biological analysis.*

*31. The microarray analysis system of claim 25, wherein the calibration scale is supported on the substrate.*

*32. The microarray analysis system of claim 25, wherein the information is transmitted via the internet.*

*33. The microarray analysis system of claim 25, wherein the database is integral to the analysis module.*

*34. The microarray analysis system of claim 25, wherein the chemical compound microarray further comprises an array of immobile target compounds.*

*35. The microarray analysis system of claim 34, wherein introduction of an amount of analyte compound initiates a color change of the target compounds.*

*36. The microarray analysis system of claim 35, wherein the color change of the target compound is within a gradient spectrum of a reference color present on the calibration scale.*

*37. The microarray analysis system of claim 36, wherein the color of the target compound relative to the gradient is correlated to the amount of the analyte compound.*

*38. The method of claim 25, wherein the chemical compound microarray further comprises an array of immobile target compounds.*

*39. The method of claim 38, wherein introduction of an amount of analyte compound initiates a color change of the target compounds.*

*40. The method of claim 39, wherein the color change of the target compound is within a gradient spectrum of a reference color present on the calibration scale.*

*41. The method of claim 40, wherein the color of the target compound relative to the gradient is correlated to the amount of the analyte compound.*

* * * * *